United States Patent
Harrington et al.

(10) Patent No.: US 7,593,562 B2
(45) Date of Patent: Sep. 22, 2009

(54) METHOD AND SYSTEM FOR COMPUTER AIDED DETECTION (CAD) CUED READING OF MEDICAL IMAGES

(75) Inventors: Scott Harrington, Etobicoke (CA); Wido Menhardt, Los Gatos, CA (US); Daoxian Heidi Zhang, Los Gatos, CA (US)

(73) Assignee: Carestream Health, Inc., Rochester, NY (US)

( * ) Notice: Subject to any disclaimer, the term of this patent is extended or adjusted under 35 U.S.C. 154(b) by 619 days.

(21) Appl. No.: 10/528,665

(22) PCT Filed: Sep. 24, 2003

(86) PCT No.: PCT/CA03/01391

§ 371 (c)(1), (2), (4) Date: Sep. 16, 2005

(87) PCT Pub. No.: WO2004/029851

PCT Pub. Date: Apr. 8, 2004

(65) Prior Publication Data

US 2006/0122467 A1    Jun. 8, 2006

Related U.S. Application Data

(60) Provisional application No. 60/413,055, filed on Sep. 24, 2002.

(51) Int. Cl.
*G06K 9/00* (2006.01)

(52) U.S. Cl. .................. 382/141; 382/128; 382/132; 600/300; 128/920

(58) Field of Classification Search .............. 382/128, 382/132, 133, 156, 162, 169, 172, 194, 196, 382/203, 209, 232, 237, 240, 243, 248, 260, 382/268–295, 302, 132.141; 600/408, 409, 600/300; 378/37, 28; 707/102; 356/443; 250/453.11; 128/920
See application file for complete search history.

(56) References Cited

U.S. PATENT DOCUMENTS

| | | | |
|---|---|---|---|
| 6,058,322 A | 5/2000 | Nishikawa et al. | |
| 6,246,782 B1 | 6/2001 | Shapiro et al. | |
| 7,054,473 B1 * | 5/2006 | Roehrig et al. | 382/128 |
| 2002/0076091 A1 | 6/2002 | Wang | |
| 2002/0097902 A1 * | 7/2002 | Roehrig et al. | 382/132 |
| 2002/0114506 A1 | 8/2002 | Hiroi et al. | |

FOREIGN PATENT DOCUMENTS

EP    0 487 110    10/1999

OTHER PUBLICATIONS

Bin Zheng et al., Soft-Copy Mammographic Readings with Different Computer-assisted Detection Cuing Environments: Preliminary Findings, Radiology 2001, Breast Imaging, pp. 633-640.

* cited by examiner

*Primary Examiner*—Sheela C Chawan

(57) ABSTRACT

A method and system for Computer Aided Detection (CAD) of abnormalities in X-ray images in which the features and/or criteria used in the CAD analysis are displayed as coded descriptors on the digital image of the X-ray to provide an indication to a user of the basis underlying the identification of a particular abnormality therefore increasing the reliability of a diagnosis established by the user.

18 Claims, 7 Drawing Sheets

| CAD STEP | CRITERIA / FEATURES | CODED DESCRIPTOR TVPE | CODED DESCRIPTOR TVPE | REGION ID |
|---|---|---|---|---|
| ⋮ | ⋮ | ⋮ | ⋮ | ⋮ |
| 1 | BRIGHTNESS OF PIXELS | ALPHA-NUMERIC | "BRIGHTNESS HIGH" | R2 |
| 2 | NUMBER OF SPICULES | ALPHA-NUMERIC | NUMBER OF SPICULES HIGH | R4 |
| 3 | PROBABILITY OF DISEASE | ANALOG | △ (RED TRIANGLE) ( HIGH > 90% ) | R5 |
| ⋮ | ⋮ | ⋮ | ⋮ | ⋮ |

FIG. 3

METHOD AND SYSTEM FOR COMPUTER AIDED DETECTION (CAD) CUED READING OF MEDICAL IMAGES

This application claims priority on PCT International Application No. PCT/CA2003/001391 filed on Sep. 24, 2003 and published as WO 2004/029851, which claims priority from U.S. provisional application 60/413,055 filed Sep. 24, 2002 entitled "Method for Computer Aided Detection (CAD) Cued Reading of Medical Images".

TECHNICAL FIELD

The present invention relates to the field of Computer-Aided Detection (CAD) of abnormalities in X-ray films.

BACKGROUND OF THE INVENTION

X-ray films to be analyzed by Computer Aided Detection (CAD) are scanned by a digitizer station, and converted into digital format. Computer algorithms analyze the digital images and identify features of the digitized image such as suspicious areas in the case of mammography for example.

In the diagnosis process, current methods require that the physician first reads the mammograms without the aid of a computer. Once the physician has noted her findings, she turns on computer monitors that show suspicious areas identified by CAD analysis as an overlay over the digitized versions of the mammogram. The suspicious areas may confirm the findings of the physician. Or, the physician may be prompted to re-examine areas she had not found to be suspicious, but which were highlighted by the computer.

These suspicious areas are typically highlighted using "marks" on the images indicating the vicinity of a suspicious region. In the event that these CAD marks disagree with the physician's findings, she is then confronted with the task of determining why her findings differ from the CAD marks. Often, the CAD mark is due to some artifact or other obvious attribute of the image. Other times, the reason for the mark is more subtle. It can be very unsettling for the physician if the reason for the discrepancy cannot be easily determined.

Current systems attempt to mark regions that the computer "thinks" are cancerous. Therefore, great care must be taken to train the CAD system to only mark regions that have a high probability of being cancerous, and minimize the number of false-positives. The trade-off is that this results in the computer not marking a significant percentage of regions that are potentially cancerous (false-negatives). Current systems balance this tradeoff by establishing a "likelihood" for whether a detected region is cancerous. The threshold for this likelihood is then set to optimize performance on the ROC (receiver operating characteristics) curve for sensitivity vs. specificity. In addition, certain heuristics can be added to discard potential false-positives. Any detected region which does not score high enough on the likelihood scale, or which fails certain heuristic tests, is discarded and no mark is shown.

This leads to what is referred to as the "second read" model, based on the idea of using two independent analyses of the images (one by a human and one by the computer) to improve the chances of correctly identifying potential cancers in the image. The human correctly identifies a certain percentage of the suspicious regions, the computer correctly identifies a certain percentage (some overlapping, some not), with a final result being a higher overall detection rate.

A major downside to this approach is that it requires the physician to read each image twice: once with the CAD marks and once without. A second downside is that once the physician views the CAD results, the human and CAD results may disagree. It is then the responsibility of the physician to determine the reason for the discrepancy and to determine whether the computer or the physician is correct. Even though some systems may display the CAD results with a probability or likelihood that a suspicious area is cancerous (see for example Zheng et al. 2001, Radiology, 221(3):633-640 and U.S. Patent Applications No. 20020097902, and 20020076091), the CAD results displayed by the computer remain of a "pass/fail" nature and the physician may often struggle in determining the underlying reason for the discrepancy.

SUMMARY OF THE INVENTION

In one aspect of the present invention there is provided a method for displaying results of a computer aided detection (CAD) analysis of a digital or digitized image of a tissue for increasing the accuracy of diagnosis by a user/physician. The method comprises analyzing a digital image of an X-ray film using CAD analysis to produce CAD results, the CAD analysis being capable of detecting regions of the digital image having a greater than zero probability for the presence of one or more abnormalities, and generating one or more coded descriptors of the CAD results, the coded descriptors being associated with the regions detected by CAD analysis and providing information on one or more criteria and/or features used in the CAD analysis. In this manner, when the CAD results are displayed with the associated coded descriptors, the user may evaluate the criteria that were used by the CAD algorithm to arrive at an identification of an abnormal region to enhance the accuracy of his/her diagnosis.

In an embodiment of the method of the present invention the user/physician may use the coded descriptors at different stages of the visual analysis of the X-ray film or its digital image. For example the physician may first visually analyze the X-ray image without the coded descriptors and establish a diagnosis based on the characteristics of the features of the regions he/she considers suspicious. She may then look at the image with the coded descriptors and compare the basis of her diagnosis with that of the CAD analysis. This way, the physician can validate his/her diagnosis and he/she can also validate the basis of his/her diagnosis.

In another embodiment the physician may visually analyze the X-ray image to establish a diagnosis while consulting simultaneously the corresponding image with the coded descriptors and/or with conventional CAD results displayed. Using this sequence of event the practitioner may first look at the coded descriptor(s) and/or conventional CAD markers in a suspicious region of the image and than look at the same region in the image without the coded descriptor and/or CAD markers and establish a diagnosis partly based on the information provided by the coded descriptors. Thus the visual diagnosis can be guided (cued) by the coded descriptors.

The use of the coded descriptors advantageously improves visual diagnosis by helping in validating the final result of the analysis, that is, the determination of whether a suspicious region is indeed abnormal (cancerous) and by providing the basis for the CAD analysis that can be compared to the basis of the diagnosis established by the practitioner. The method of the present invention thereby contributes to lower the number of false positives or false negatives associated with X-ray analysis.

BRIEF DESCRIPTION OF THE DRAWINGS

Further features and advantages of the present invention will become apparent from the following detailed description, taken in combination with the appended drawings, in which:

FIG. 3 is a schematic representation of an internal storage table in which information related to coded descriptors is stored;

It will be noted that throughout the appended drawings, like features are identified by like reference numerals.

DETAILED DESCRIPTION OF THE PREFERRED EMBODIMENT

In an aspect of the present invention there is provided a system and a method for analyzing X-ray films such as mammograms using Computer Aided Detection (CAD) and for presenting the results to a user such as to indicate some or all of the criteria used by a CAD algorithm to estimate the likelihood that an abnormality in an X-ray film, indicative of a disease state in the tissue, is present. This method can assist a physician in determining the likelihood of a suspicious region being indicative of the presence of cancer or other diseases. The manner in which the results are displayed provides a simplified visual representation of the complex logic used by the computer to determine the likelihood of disease as will be further described below.

While the description of the method of the present invention will refer to analysis of mammograms for the detection of cancerous lesions, it will be appreciated that the method may also be applied to other types of diagnosis imaging methods amenable to CAD analysis.

Figure 1:
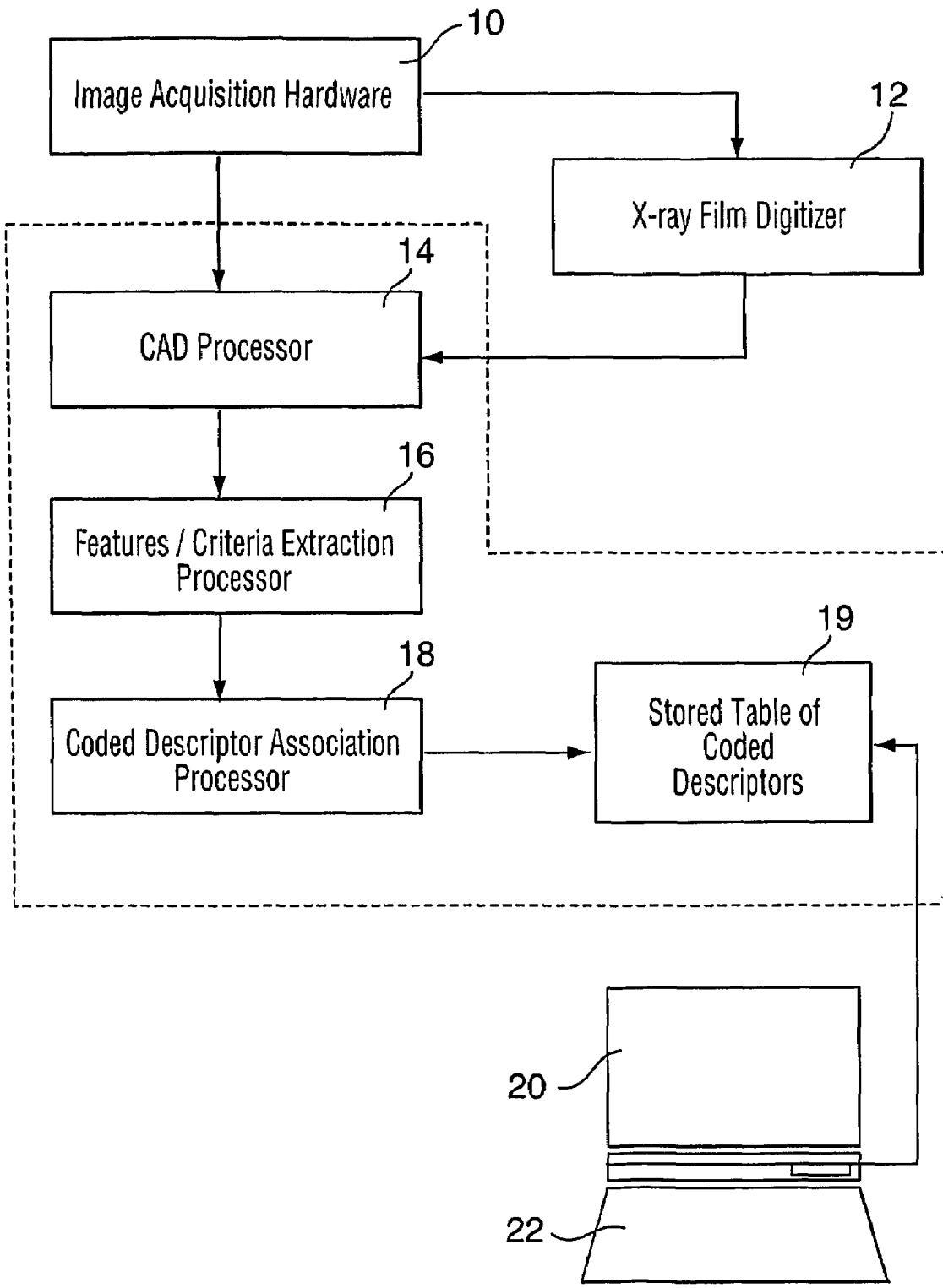
FIG. 1 is a schematic representation of an embodiment of the system of the present invention.

A schematic representation of the system is provided in FIG. 1 and comprises image acquisition hardware 10, optionally an X-ray film digitizer 12, a CAD processor 14, a feature/criteria extraction processor 16, a coded descriptors-feature/criteria association processor 18, an internal storage table 19 to store information associated with coded descriptors, a display 20 such as a computer screen and a user interface 22 such as a keyboard or a mouse. The X-ray film digitizer is optional since diagnosis procedures such as mammography can be obtained digitally.

Figure 2:
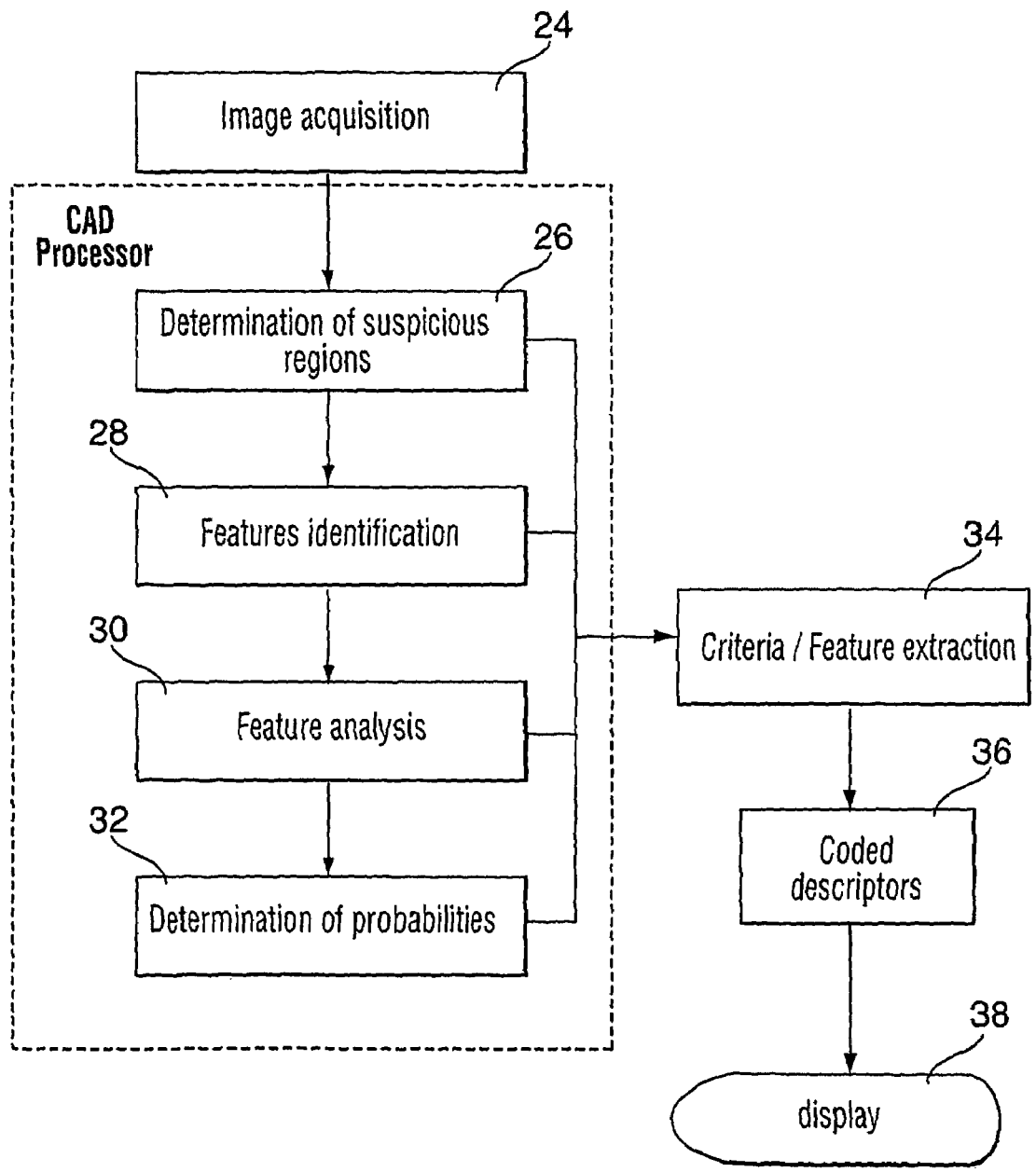
FIG. 2 is a flow chart representation of an embodiment of the method of the present invention in which the X-ray image is analyzed by CAD and coded descriptors are displayed with the image.

FIG. 2 is a schematic representation of the steps involved in an embodiment of the method of the present invention. A digitized X-ray film or a digital radiogram such as a digital mammogram is first acquired at 24 and provided to the CAD processor 14 to be analyzed by a CAD algorithm. It will be appreciated that a step of digitization may first be carried out if an analog X-ray film is originally provided. The CAD algorithm first performs a series of image processing steps at 26 to detect potentially suspicious regions (exhibiting probable abnormalities). This can be achieved, for example, by using spatial bandpass filters of different sizes to detect the presence of masses or by using high pass filters to highlight bright but small areas of the image indicative of the presence of calcifications.

After detecting the suspicious regions, features of the regions are identified at 28 for each suspicious region. The identified features are then analyzed at 30 and the results of the analysis are used to determine, at 32, the likelihood (probability) that the identified region is characteristic of a disease such as cancer Each step of the CAD analysis may rely on distinct criteria or feature characteristics to determine whether or not a region is anomalous. Thus step 26 in which the CAD algorithm determines whether a region is "suspicious" may rely on the intensity of the pixels in the region while step 30 of feature analysis may take into account the number of spicules within the suspicious region for example. The criteria/features characteristics used in the CAD analysis process are extracted at 34 and are associated with corresponding coded descriptors at 36. The coded descriptors may then be displayed with the X-ray image at 38 on an appropriate display medium such as a computer screen or a printed report.

The coded descriptors, in addition to provide information about the criteria/feature characteristics, may also identify the step within the CAD analysis at which the criteria/features characteristics was used. Referring to FIG. 3, the data, associated with a coded descriptor and specific for each step of the CAD analysis, can be stored in table 19 which can be accessed to retrieve the information The steps of the CAD analysis can be represented by numbers. For example the step of "determination of suspicious regions" (referral number 26 in FIG. 2) can be identified as step number one (1). The retrieval may be by default i.e. the information that is retrieved from table 19 may be predetermined. For example the coded descriptor (s) corresponding to the step of feature analysis may be automatically displayed with the CAD results. It will be appreciated that coded descriptors associated with different steps of the CAD analysis can be simultaneous displayed. Alternatively, the user may specify the information to be retrieved.

Thus the information regarding the contribution of different features to the CAD results associated with coded descriptors and displayed on the X-ray digital image provide the physician with an appreciation of the criteria used by the CAD algorithm to arrive at the determination of whether a suspicious region is cancerous or not. Different features of suspicious regions in X-ray films have different relevance depending on the type of CAD analysis performed and the type of disease. In the case of, cancerous masses, one criterion for determining whether a region is cancerous is the amount of "spicules" present in a mass. In this respect, mammography films can present significant challenges in visualizing subtle spiculated masses or other features of suspicious regions and displaying coded descriptors associated with such regions facilitates the diagnosis.

U.S. Pat. No. 6,246,782 to Shapiro et al., which is incorporated herein by reference, describes a system for automated detection of cancerous masses in mammograms. The features extracted from suspicious regions may include size, brightness, location, density, number and length of spicules and the like. These features can be analyzed by several different methodologies that are well known in the art. For example, U.S. Pat. No. 6,246,782 describes the use of such features as inputs for neural networks that are trained based on a set of data using images containing certain cancerous and noncancerous features. The system thus "learns" which features and combinations of features are indicative of a potential cancer.

Once the analysis of the likelihood of a suspicious region being cancerous is completed, the results are translated into a form that can be interpreted by a human reader. Each suspicious region is highlighted in the CAD display. Typically, this display will be either a computer monitor or printed report. The highlighting of the regions may be achieved in a number of ways, including but not limited to showing an outline of the suspicious region or highlighting it with a filled transparent colored overlay.

Figure 4:
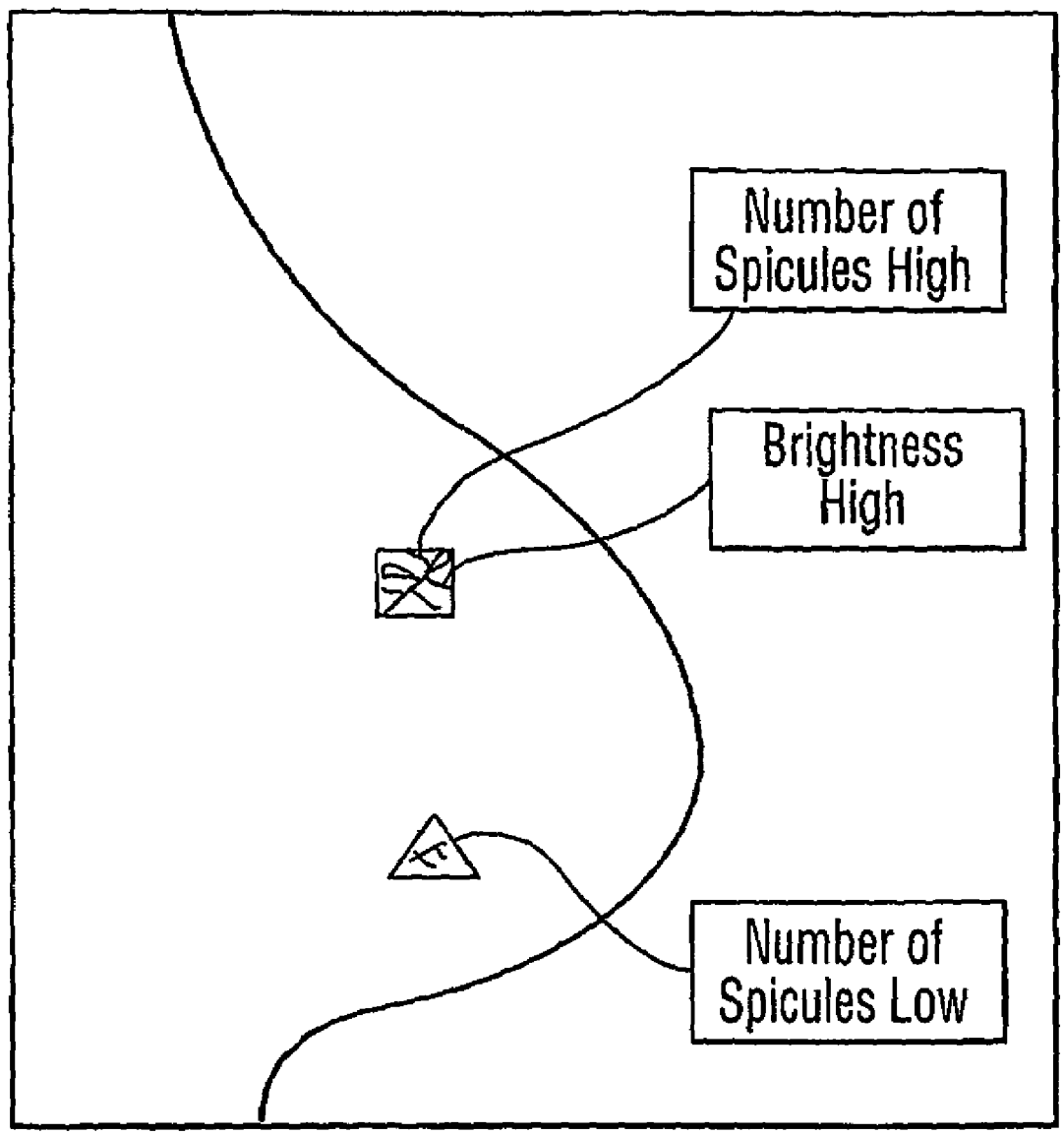
FIG. 4 is a schematic representation of an embodiment of a display of a digital image of a mammogram with coded descriptors.

For example, if a neural network, after analysis of a suspicious region, detects a region as having a certain probability of being cancerous in part based on the number of spicules, the system may display a coded descriptor, associated with the region, which highlights the spicules within the region. Alternatively, and as depicted in FIG. 4, the coded descriptor may be a user readable sentence describing the criteria/features characteristics of the suspicious region. Thus if the physician had previously rejected this region, she or he would be prompted to re-examine the region by paying particular attention to the highlighted spicules as a possible indication of the presence of cancer. The choice of the coded descriptor to be displayed can be based on the importance of the associated feature in the CAD analysis or it can be predetermined by the user.

As mentioned previously, the user may choose to display one or more coded descriptor of his or her choice, using a user interfaces provided the associated features were used in the CAD analysis. Also, information on the weight given to different features in establishing the CAD results can be extracted from the appropriate data fields in computerized data tables.

The coded descriptor may also be associated with a descriptive sentence in medical terms of the abnormality within a suspicious region. The descriptive sentence can be determined by features analysis in the CAD algorithm and stored in table 19. Non-limiting examples of entences include "nodules irregular margins", "parenchymal distortion" and the like.

Thus by coded descriptor it is meant any distinguishable form of visual marker or display that can be associated with or is indicative of the features and/or criteria on which the CAD results are based and of the step in the CAD analysis at which the features/criteria were used. Furthermore the coded descriptor may be indicative of the likelihood of the presence of disease state. Embodiments of coded descriptors may include highlighting of features, use of analog symbols (geometric shapes) and displaying of alpha-numeric information (such as the Breast Imaging Reporting and Data System, BI-RADS) and combination thereof. The display of coded descriptors may be on a computer screen or on a printed report. The coded descriptors may be color coded to reflect, for example, the probability that an abnormality in the image is indicative of disease state. A color code may also be used to identify the step in the CAD analysis corresponding to the coded descriptor. Furthermore, in a preferred embodiment, the coded descriptors are displayed with varying shades of the same color each shade corresponding to a predetermine level of probability that the suspicious region is indicative of disease state. Thus a given color, for example green, would indicate that the information conveyed is the probability and the shade of green would indicate the actual level of the probability as determined by the CAD analysis.

Highlighting may also take the form of dynamically changing degrees of intensity or transparency. That is to say the highlighting can be "faded int" and "faded out" to help the physician in locating the region and analyzing the features with varying degrees of highlighting without the need of toggling the CAD display back and forth.

Micro-calcification cluster (MCC) detection can also be indicative of the presence of cancer. MCC can be defined as consisting of 3 or more calcifications (shown as bright spots on the image). The present invention provides a means for highlighting and enumerating the calcifications found for each cluster. In one embodiment, the system presents to the user all regions found containing bright spots with potential cancerous indications. Color-coding of a border surrounding each region is used to indicate whether the CAD system found it likely to be indicative of cancer. Furthermore, each bright spot within the region is highlighted. In this manner, the system can present to the user all suspicious regions. Although many false positives may be present, by highlighting the features used to make the determination of whether the region is a MCC, the physician can easily dismiss the false positives. Furthermore, by including regions with fewer than 3 bright spots (but color coding their borders differently to indicate the CAD system did not find them highly suspicious), the physician can quickly confirm whether the computer's determination that a potentially suspicious region is harmless is correct.

In another embodiment of the invention, the display of the coded descriptors can be adapted to the experience of the user in reading mammograms or in using CAD.

Other means of highlighting and displaying the coded descriptors may be used as would be obvious to one skilled in the art.

Figure 5:
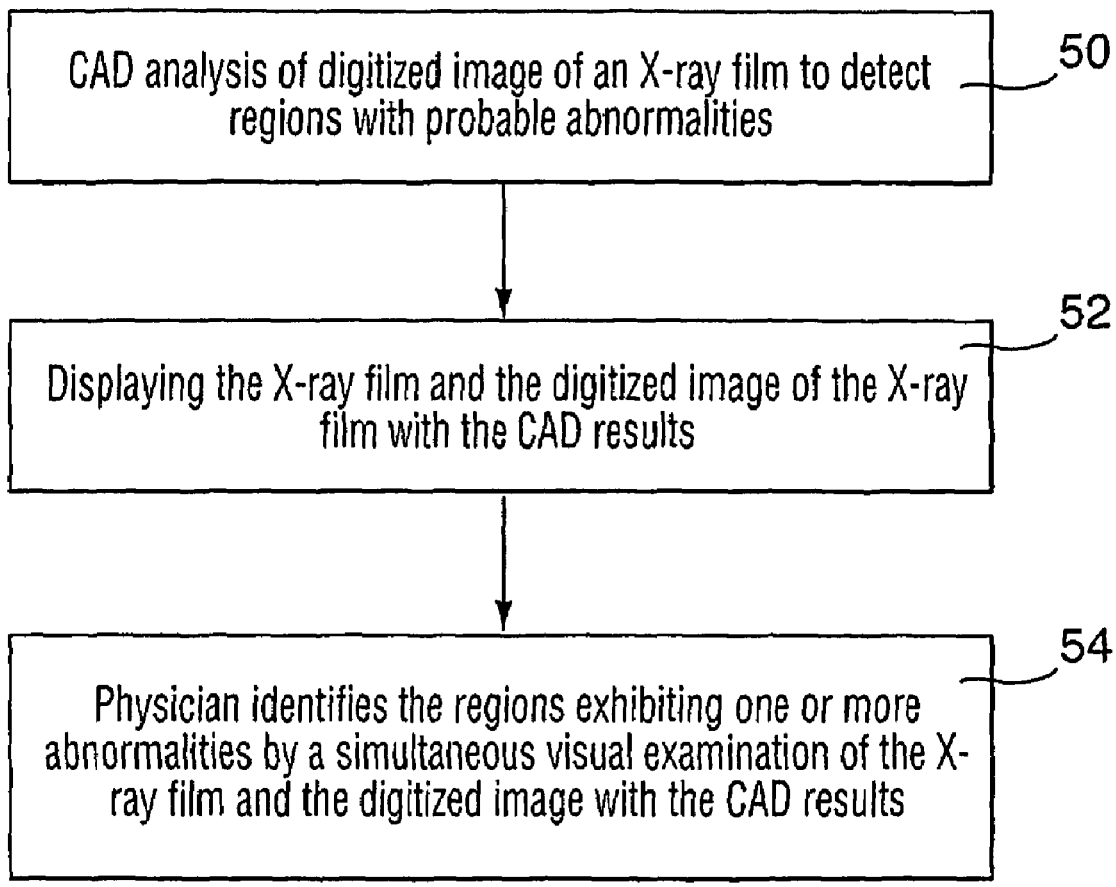
FIG. 5 is a flow chart representation of an embodiment of the present invention describing a method for detecting and identifying, in an X-ray film analyzed by CAD, regions with abnormalities by simultaneously analyzing the X-ray film and a digitized image of the X-ray film with the CAD results.

CAD image analysis and coded descriptors can be used by the physician at different stages of the diagnosis process for the purposes of enhancing the reliability of the diagnosis. Referring to FIG. 5 conventional CAD analysis results obtained at 50 from the analysis of an X-ray film such as a mammogram (i.e. without the coded descriptors) can be displayed at 52 such that both the image (or film) without the CAD results and the corresponding image with the CAD results can be viewed simultaneously at 54 by the physician. In this manner, the physician can perform a visual examination of the film to identify abnormalities while referring to the image with the CAD results to guide his/her analysis.

Figure 6:
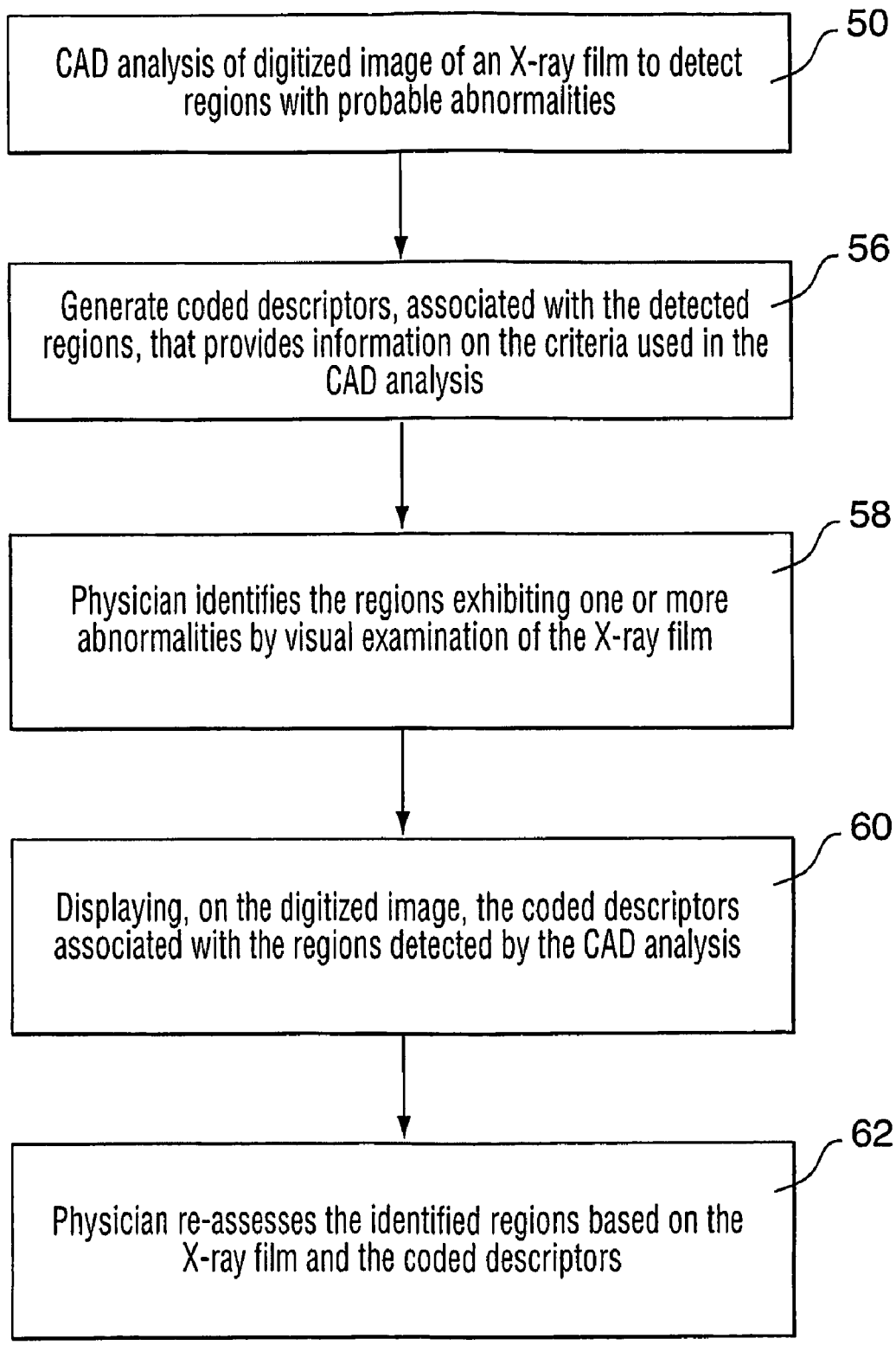
FIG. 6 is a flow chart representation of an embodiment of the present invention describing a method for detecting and identifying, in an X-ray film, regions with abnormalities using coded descriptors.

In another embodiment of the method and referring to FIG. 6, the CAD analysis 50 is first performed and coded descriptors are generated at 56. The physician can then first analyze the X-ray film at 58 and subsequently analyze the corresponding digital image displayed with coded descriptors at 60. The physician can then compare the basis of his/her diagnosis with that of the CAD analysis and possibly re-assess at 62 the type of abnormality (cancerous or not) in the suspicious regions. However, because the coded descriptors convey information on the criteria used by the CAD analysis, the physician is able to make a logical assessment as to the validity of the computer results based on clearly defined features of the suspicious regions.

Figure 7:
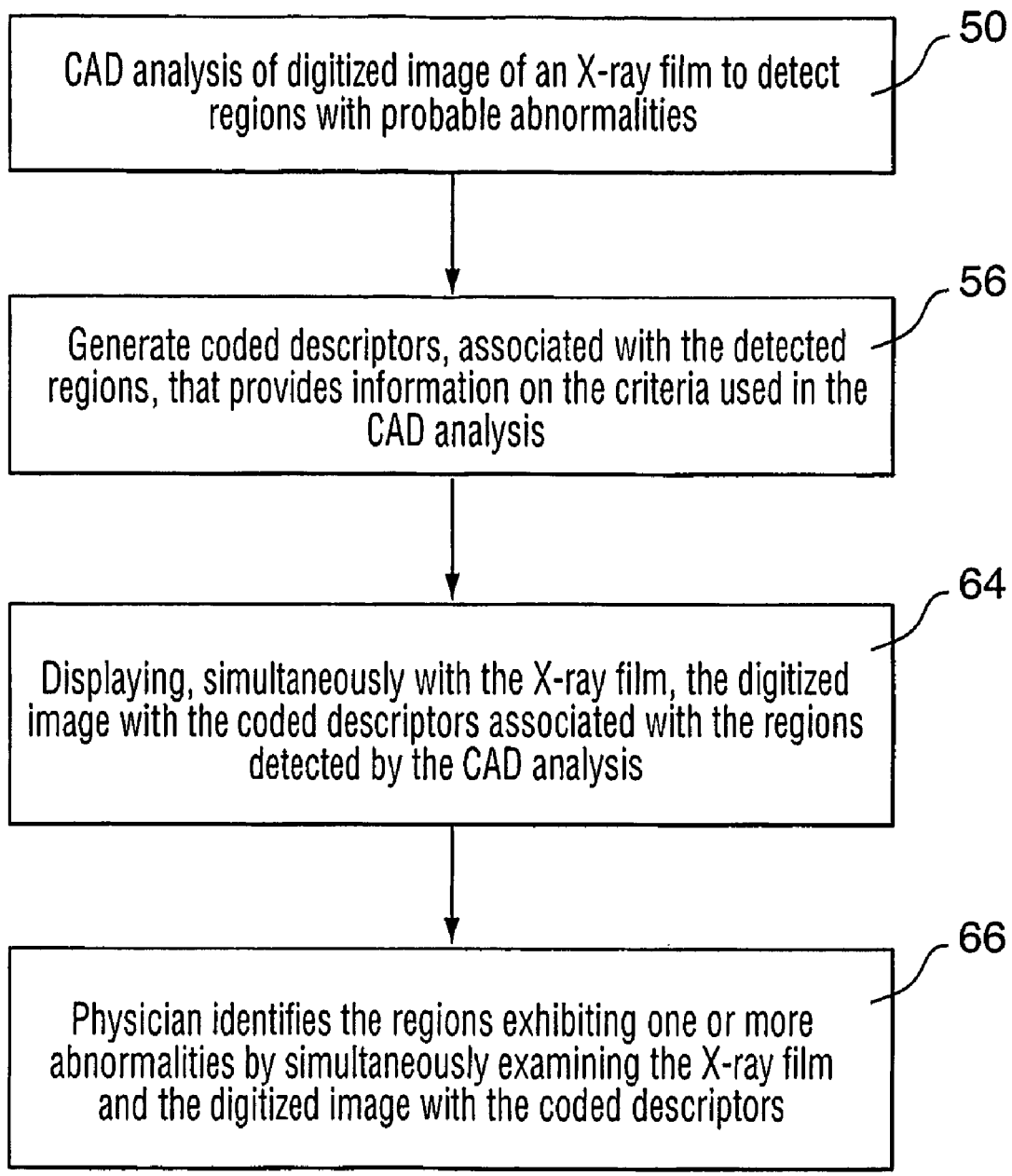
FIG. 7 is a flow chart representation of an embodiment of the present invention describing a method for detecting and identifying, in an X-ray film, regions with abnormalities by simultaneously analyzing the X-ray film and coded descriptors.

In yet another embodiment and referring to FIG. 7, the X-ray film and the corresponding digital image, displayed with coded descriptors, are simultaneously displayed at 64 and simultaneously analyzed at 66 by the physician who is then assisted in her analysis of the X-ray film by the coded descriptors.

It will be appreciated that the above two embodiments can be performed using any combination of displays which can include alternators and light boxes to view analog X-ray films as well as monitors such as computer screens to view the digital image of the X-ray or a digital mammograms as well as the CAD results and the coded descriptors. The different images may be displayed simultaneously or sequentially. Thus for example, the computer screen may display both the digital image with the coded descriptors with the digital image without the descriptors. Also it is possible to display only part of a digital image with or without the coded descriptors.

It will also be appreciated that the threshold used for determining whether a suspicious region is cancerous can be set low so that substantially all the suspicious regions are identified together with coded descriptors. The CAD system can provide a first read with the physician scanning through each highlighted region and then making a determination regarding the likelihood of cancer based on the coded descriptors and the features on the image. In this manner, the physician can far more easily understand why a region is marked, and more quickly make a correct judgment regarding whether the marked region is indeed suspicious enough to require further analysis.

The embodiment(s) of the invention described above is(are) intended to be exemplary only. The scope of the invention is therefore intended to be limited solely by the scope of the appended claims.

The invention claimed is:

1. A method for displaying results of a computer aided detection (CAD) analysis of a digital image, the method comprising:
   i) analyzing the digital image using CAD analysis to identify one or more CAD-detected abnormalities;
   ii) generating one or more coded descriptors for said CAD-detected abnormalities wherein said coded descriptors provide information on one or more criteria used by said CAD analysis to identify said CAD-detected abnormalities; and
   iii) displaying said digital image with the one or more coded descriptors;
   wherein said one or more coded descriptors is selected from visual markers, alpha-numeric information or a combination thereof; and
   wherein said visual markers can be displayed with varying degrees transparency.

2. The method as claimed in claim 1 wherein said digital image is a digitized image of an X-ray film.

3. The method as claimed in claim 1 wherein said digital image is a digital mammogram.

4. The method as claimed in claim 1 further comprising visually analyzing said digital image to identify one or more user-detected abnormalities, said visual analysis being performed before said step of displaying and wherein said user-detected abnormalities are re-assessed based on said information provided by said coded descriptors.

5. The method as claimed in claim 4 wherein said digital image is a digitized image of an X-ray film and wherein said visual examination is performed on said X-ray film.

6. The method as claimed in claim 1 further comprising visually analyzing said digital image to identify one or more user-detected abnormalities said visual examination being performed with said coded descriptors being displayed simultaneously such that a user can refer to said coded descriptors while performing said visual analysis.

7. The method as claimed in claim 6 wherein said digital image is a digitized image of an X-ray film and wherein said visual examination is performed on said X-ray film.

8. The method as claimed in claim 1 wherein said one or more coded descriptor displayed in the image is selected by a user.

9. The method as claimed in claim 1 wherein said coded descriptors also provide information on probability that said CAD-detected abnormalities are indicative of a disease state.

10. The method as claimed in claim 1 wherein the alpha-numeric information is based on Breast Imaging Reporting and Data System (BI-RADS).

11. The method as claimed in claim 1 wherein said alpha-numeric information is a sentence describing in medical terms said CAD-detected abnormalities.

12. The method as claimed in claim 1 wherein said visual markers comprise border delineations of regions.

13. The method as claimed in claim 1 wherein said visual markers comprise one or more highlighted feature used by CAD for determining likelihood of abnormality.

14. The method as claimed in claim 13 wherein said highlighted feature is selected from size, brightness, location, density, number and length of spicules.

15. The method as claimed in claim 13 wherein said highlighted feature comprise individual calcifications within a micro-calcification cluster.

16. The method as claimed in claim 1 wherein said visual markers are color coded according to said probability that the CAD-detected abnormalities are indicative of a disease state.

17. The method as claimed in claim 16 wherein said visual markers are of a same color and wherein a level of probability is indicated by a predetermined shade of said same color.

18. The method as claimed in claim 1 wherein said degrees of transparency to display the visual markers vary dynamically.

* * * * *